US007883785B2

(12) United States Patent
Stössel et al.

(10) Patent No.: US 7,883,785 B2
(45) Date of Patent: *Feb. 8, 2011

(54) RHODIUM AND IRIDIUM COMPLEXES

(75) Inventors: Philipp Stössel, Frankfurt (DE); Ingrid Bach, Bad Soden (DE); Hubert Spreitzer, Viernheim (DE)

(73) Assignee: Merck Patent GmbH (DE)

( * ) Notice: Subject to any disclaimer, the term of this patent is extended or adjusted under 35 U.S.C. 154(b) by 1520 days.

This patent is subject to a terminal disclaimer.

(21) Appl. No.: 10/525,396

(22) PCT Filed: Aug. 14, 2003

(86) PCT No.: PCT/EP03/09015

§ 371 (c)(1),
(2), (4) Date: Mar. 4, 2005

(87) PCT Pub. No.: WO2004/026886

PCT Pub. Date: Apr. 1, 2004

(65) Prior Publication Data

US 2006/0127696 A1   Jun. 15, 2006

(30) Foreign Application Priority Data

Aug. 24, 2002   (DE) ................. 102 38 903

(51) Int. Cl.
   H01L 51/54   (2006.01)
   C09K 11/06   (2006.01)
   H02N 6/00   (2006.01)

(52) U.S. Cl. .............. 428/690; 428/917; 313/504; 313/506; 252/301.16; 252/519.3; 257/40; 257/102; 257/E51.044; 546/2; 546/4; 546/10; 136/243

(58) Field of Classification Search ........... 428/690, 428/917; 313/504, 506; 257/40, E51.044, 257/102, 103; 546/2, 4, 10; 252/301.16, 252/301.18, 301.24, 301.32, 519.3
See application file for complete search history.

(56) References Cited

U.S. PATENT DOCUMENTS

| 4,539,507 | A | 9/1985 | VanSlyke et al. |
| 5,151,629 | A | 9/1992 | VanSlyke |
| 5,621,131 | A | 4/1997 | Kreuder et al. |
| 5,679,760 | A | 10/1997 | Mullen et al. |
| 6,653,438 | B1 | 11/2003 | Spreitzer et al. |
| 7,094,897 | B2 * | 8/2006 | Stossel et al. ............. 546/4 |
| 2001/0019782 | A1 * | 9/2001 | Igarashi et al. ............. 428/690 |
| 2003/0059646 | A1 * | 3/2003 | Kamatani et al. ........... 428/690 |
| 2003/0068526 | A1 | 4/2003 | Kamatani et al. |
| 2003/0068536 | A1 * | 4/2003 | Tsuboyama et al. ......... 428/704 |
| 2004/0054152 | A1 | 3/2004 | Meerholz et al. |
| 2004/0077862 | A1 | 4/2004 | Stossel et al. |
| 2004/0133004 | A1 | 7/2004 | Stossel et al. |
| 2004/0138455 | A1 | 7/2004 | Stossel et al. |

FOREIGN PATENT DOCUMENTS

| DE | 101 09 027 | 9/2002 |
| DE | 101 53 450 | 5/2003 |
| DE | 102 15 010 | 10/2003 |
| EP | 07 070 20 | 4/1996 |
| EP | 0 842 208 | 5/1998 |
| EP | 1 028 136 | 8/2000 |
| EP | 1 348 711 | 10/2003 |
| GB | 0206356.8 | 3/2002 |
| GB | 2 404 380 | 2/2005 |
| WO | WO-92/18552 | 10/1992 |
| WO | WO-00/22026 | 4/2000 |
| WO | WO-01/34722 | 5/2001 |
| WO | WO-02/10129 | 2/2002 |
| WO | WO-02/44189 | 6/2002 |
| WO | WO 02/45466 A1 * | 6/2002 |
| WO | WO-02/060910 | 8/2002 |
| WO | WO-02/066552 | 8/2002 |
| WO | WO-02/068435 | 9/2002 |
| WO | WO-02/081488 | 10/2002 |
| WO | WO-03/079736 | 9/2003 |
| WO | WO-03/084973 | 10/2003 |

OTHER PUBLICATIONS

Lo, Shin-Chun et al., "Green Phosphorescent Dendrimer for Light-Emitting Diodes" Advanced Materials, Advanced Materials 2002, 14, No. 13-14.

Markham, J. P. et al., "High-Efficiency Green Phosphorescence From Spin-Coated Single-Layer Dendrimer Light-Emitting Diodes," Applied Physics Letters, vol. 80, No. 15, pp. 2645-2647. (Apr. 15, 2002).

\* cited by examiner

*Primary Examiner*—D. Lawrence Tarazano
*Assistant Examiner*—Michael Wilson
(74) *Attorney, Agent, or Firm*—Connolly Bove Lodge & Hutz LLP

(57) ABSTRACT

The present invention describes novel organometallic compounds which are phosphorescent emitters. Such compounds can be used as active components (=functional materials) in a variety of different applications which can in the widest sense be considered part of the electronics industry.

The compounds of the invention are described by the formulae (I), (Ia), (II) and (IIa).

20 Claims, No Drawings

RHODIUM AND IRIDIUM COMPLEXES

RELATED APPLICATIONS

This application is a national stage application (under 35 U.S.C. 371) of PCT/EP2003/009015 filed Aug. 14, 2003 which claims benefit to German application 102 38 903.9 filed Aug. 24, 2002.

Organometallic compounds, especially compounds of the $d^8$ metals, will in the near future be employed as active components (=functional materials) in a variety of different applications which can in the widest sense be considered part of the electronics industry.

In the case of the organic electroluminescence devices based on organic components, (for general description of the structure cf. U.S. Pat. No. 4,539,507 and U.S. Pat. No. 5,151,629) or their individual components, viz. organic light-emitting diodes (OLEDs), introduction onto the market has already occurred, as the car radios with "organic display" obtainable from Pioneer demonstrate. Further such products will be introduced shortly. Nevertheless, significant improvements are still necessary here in order for these displays to compete effectively with or to surpass the liquid crystal displays (LCDs) which currently dominate the market.

A development in this direction which emerged some years ago is the use of organometallic complexes which display phosphorescence instead of fluorescence [M. A. Baldo, S. Lamansky, P. E. Burrows, M. E. Thompson, S. R. Forrest, Applied Physics Letters, 1999, 75, 4-6].

For reasons of theoretical spin statistics, an up to four-fold increase in the energy and power efficiency can be achieved when using organometallic compounds as phosphorescent emitters. Whether this new development will become established depends greatly on whether appropriate device compositions which can bring these advantages (triplet emission=phosphorescence, compared to singlet emission=fluorescence) to OLEDs, too. Important conditions for practical use are, in particular, a long operational life, a high stability to heat and a low use and operational voltage in order to make mobile applications possible.

In addition, an efficient chemical route to the corresponding organometallic compounds has to be available. Organorhodium and organoiridium compounds are of particular interest here. In the case of these compounds, it is of particularly critical importance that an efficient route to appropriate derivatives is possible in view of the price of rhodium and iridium.

A weak point of the phosphorescent emitters described hitherto is their poor solubility. Thus, hybrid device structures which combine the advantages of the "small molecule" OLEDs with those of polymeric OLEDs (PLEDs) have been evaluated, in particular recently. It is of particular importance here that the compounds be applied from solution. A number of possibilities have been described for this purpose: (a) application of pure layers of "small molecules" or triplet emitters, and (b) introduction of blends (=mixtures) of these into polymeric or low molecular weight matrices. Hoped-for advantages of these hybrid structures are, inter alia, the following:

Application from solution (especially by means of high-resolution printing processes) would give significant long-term advantages compared to the vacuum vapor deposition process customary at present, especially in terms of scaleability, structureability, coating efficiency and economics.

Since no polymeric triplet emitters are known at present, the use of the hybrid structure can combine the advantageous device properties of low molecular weight triplet emitters with the advantageous application methods which can be used for the polymers.

Typical phosphorescent emitters which have been reported to date are organo-metallic complexes, especially of iridium. Here, tris(phenylpyridyl) complexes and derivatives, in particular, have been reported.

However, the compounds reported hitherto are, with one exception, compounds which contain either phenylpyridine itself or phenylpyridine substituted by fluorine, methoxy or similar groups or benzo-fused phenylpyridine as ligands. These compounds generally have a low solubility in customary solvents (e.g. <2 g/l, frequently less than 1 g/l; cf. figures given in the examples).

Only P. L. Burn et al. describe a dendrimer-like derivative (Adv. Mater. 2002, 14, 975; Appl. Phys. Lett. 2002, 80, 2645) which appears to have a higher solubility. However, the publications which have appeared to date do not indicate how this compound can be obtained.

In the light of what has been said above, there are two important objectives for further progress in the field of phosphorescent OLEDs:

1. There is a great need for readily soluble triplet emitters.
2. These have to be able to be synthesized readily since, as mentioned above, the price of the "raw materials" is tremendously high.

The present invention accordingly provides 5'-mono-, 5',5"-bis- and 5',5",5'''-tris-aryl/heteroaryl-functionalized tris-orthometallated organorhodium and organoiridium compounds of the formula (I/Ia) or (II/IIa). Appropriate aryl/heteroaryl substitution makes it possible to adjust critical materials properties such as the wavelength of the phosphorescent emission, i.e. the color, the phosphorescence quantum yield and the redox and thermal stability of the emitters.

A particularly important aspect is, in particular in the context of what has been said above, that the solubility can be improved greatly by, means of the present substitution (cf., in particular, the information given in the experimental part). This is of critical importance, especially for use in the above-mentioned hybrid technology.

The class of 5'-mono-, 5',5"-bis- and 5',5",5'''-tris-aryl/heteroaryl-functionalized tris-orthometallated organorhodium and organoiridium compounds of the formula (I/Ia) or (II/IIa) is, except for the exception mentioned above, new and has not hitherto been described in the literature, but the efficient preparation of these compounds and their availability as pure substances is of great importance for a number of electrooptical applications.

As indicated above, the synthesis of such compounds has not yet been reported, so that it is difficult, even for a person skilled in the art, to reproduce the results of Paul Burn et al.

As described in the following, we have found a surprisingly simple, effective process for preparing the abovementioned new compounds.

The nearest prior art for this process is the transition metal-catalyzed C—C coupling of purely organic aryl chlorides, bromides, and iodides, especially the studies by A. Suzuki et al., A. F. Littke et al., and also by S. P. Nolan et al. Among the large number of publications relating to this type of reaction, a few selected studies may be referred to below.

A. Suzuki et al., A. F. Littke et al. and J. P. Wolf et al. describe the nickel- and palladium-catalyzed C-C coupling reaction of organic aryl halides with arylboronic acids or their esters in the presence of phosphine ligands and a base [N. Miyaura, A. Suzuki Chem. Rev. 1995, 95, 2457; A. F. Littke, C. Dai, G, C. Fu J. Am. Chem. Soc. 2000, 122, 4020; J. P.-Wolf, S. L. Buchwald Angew. Chem. 1999, 111, 2570]. Conversions of 70-99% are typically achieved in these types of reaction. The purification of the crude products is a problem, and this is frequently carried out by complicated chromatographic methods.

Apart from the above-described processes, nickel- or palladium-catalyzed C—C coupling reactions between purely organic aryl halides and arylboronic acids or their esters in the presence of nitrogen-containing ligand systems and a base have been described. Nitrogen-containing ligand systems which have been found to be useful are imidazol-2-ylidenes or their protonated form, viz. imidazolium salts, and amines [C. Zhang, J. Huang, M. L. Trudell, S. P. Nolan, J. Org. Chem. 1999, 64, 3804]. Here too, conversions of 50-99% are typically obtained using simple starting materials, with the purification of the crude products often being carried out by complicated chromatographic methods.

The transition metal-catalyzed Suzuki coupling of aryl halides bound coordinately to a metal center, i.e. organorhodium and organoiridium aryl halides, as described below is novel and has not hitherto been described in the literature.

It has surprisingly been found that the new aryl/heteroaryl-substituted organometallic compounds (I/Ia) or (II/IIa) as shown in schemes 1 and 2 are obtained reproducibly from the 5'-mono-, 5',5"-bis- and 5',5",5'"-tris-halogen-substituted tris-ortho-metallated organorhodium or organoiridium compounds (III) or (IV), i.e. from organometallic aryl halides, by means of the transition metal-catalyzed reaction with organic boronic acids or their esters in the presence of a phosphorus- or nitrogen-containing additive and a base and with appropriate choice of the reaction parameters such as reaction temperature, reaction medium, concentration and reaction times in a yield of about 90-98% and purities, if appropriate after recrystallization, of >99% as determined by NMR or HPLC without use of chromatographic purification methods (cf. examples 1-8). The preparation of the organorhodium and organoiridium compounds of the formulae (III) and (IV) is described in detail in the as yet unpublished German patent application DE 10109027.7.

The above-described process has three particular properties:

Firstly, the transition metal-catalyzed, selective 5'-mono-, 5',5"-bis- and 5',5",5'"-tri-C—C coupling of coordinately bound aryl halides of rhodium and iridium, i.e. of organorhodium and organoiridium aryl halides, is unexpected and not known in this form.

Secondly, the high conversion achieved, which is reflected in the reproducibly very good yields of isolated product, is unexpected and unique to the Suzuki coupling of coordinately bound aryl halides.

Thirdly, the resulting compounds are obtained without complicated chromatographic purification in very good purities of >99% as determined by NMR or HPLC, if appropriate after recrystallization. This is essential for use in optoelectronic components or use as intermediates for the preparation of such compounds.

As indicated above, the compounds of the invention have not been described before and are therefore new.

These compounds of the invention have the following advantages:

Appropriate substitution makes it possible to cover a large bandwidth of emission colors and positions of the energy levels. Particular mention may be made of the fact that the wide variability of aryl and heteroaryl groups enables the properties to be adjusted within a very wide range.

Appropriate side chains on the aryl or heteroaryl radicals or choice of these radicals themselves (cf. data in the experimental part) allow the solubility of the complexes produced to be increased or adjusted over a wide range without an adverse effect being exerted on the other properties. This is of particular importance because direct substitution on the directly complexing ring frequently alters the properties or makes the synthesis more difficult.

The present invention accordingly provides compounds of the formulae (I) and (II) (scheme 1), Scheme 1

Formula (I)

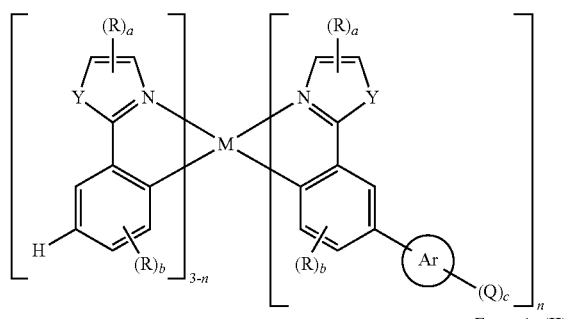

Formula (II)

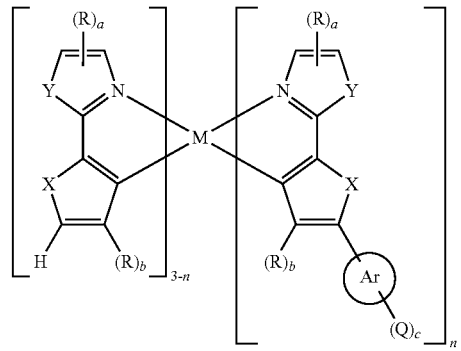

where the symbols and indices have the following meanings:

M is Rh, Ir;

X is O, S, Se;

Y is S, O, R—C=C—R, R—C=N;

R is identical or different on each occurrence and is H, F, Cl, $NO_2$, CN, a straight-chain or branched or cyclic alkyl or alkoxy group which has from 1 to 20 carbon atoms and in which one or more nonadjacent $CH_2$ groups may be replaced by —O—, —S—, —$NR^1$— or —$CONR^2$— and one or more H atoms may be replaced by F, or an aryl or heteroaryl group which has from 4 to 14 carbon atoms and may be substituted by one or more, nonaromatic radicals R; where a plurality of substituents R, either on the same ring or on the two different rings, may together form a further monocyclic or polycyclic ring system;

Ar is an aryl or heteroaryl group having from 1 to 40 carbon atoms;

Q is identical or different on each occurrence and is F, Cl, Br, I, CN, COOH, $NH_2$, OH, SH, $NO_2$, $SO_3H$, $SiR_3$ or a straight-chain or branched or cyclic alkyl or alkoxy group which has from 1 to 20 carbon atoms and in which one or more nonadjacent $CH_2$ groups may be replaced by —O—, —S—, —CO—, —COO—, —O—CO—, —$NR^1$—, —$(NR^2R^3)^+A^-$ or —$CONR^4$— and one or more H atoms may be replaced by F, or an aryl or heteroaryl group which has from 4 to 14 carbon atoms and may be substituted by one or more, nonaromatic radicals R;

$A^-$ is a singly charged anion or its equivalent;

$R^1$, $R^2$, $R^3$, $R^4$ are identical or different and are each H or an aliphatic or aromatic hydrocarbon radical having from 1 to 20 carbon atoms;

a is 0, 1, 2, 3 or 4, preferably 0, 1 or 2, b is 0, 1, 2 or 3, preferably 0 or 1;

c is from 0 to 15, preferably 0, 1, 2, 3, 4 or 5, particularly preferably 0, 1 or 2;

n is 1, 2 or 3;

with the exception of the compounds:

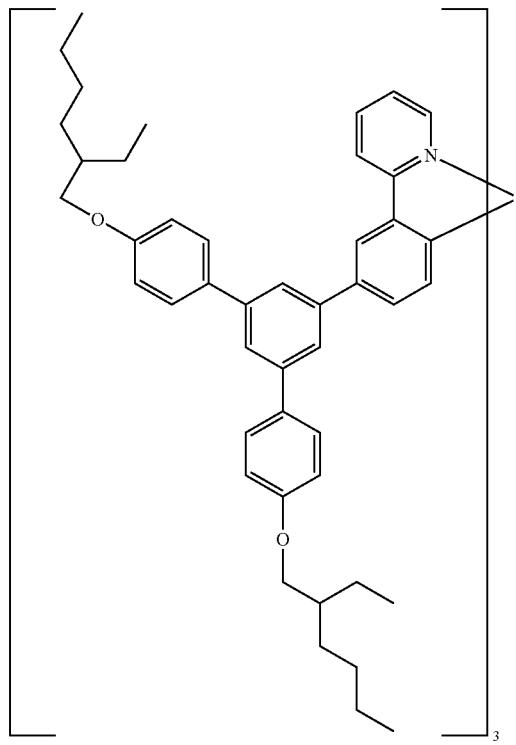

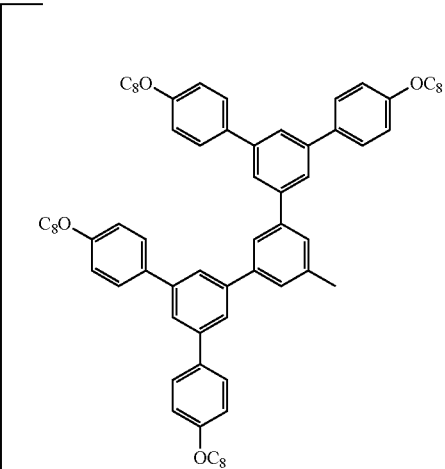

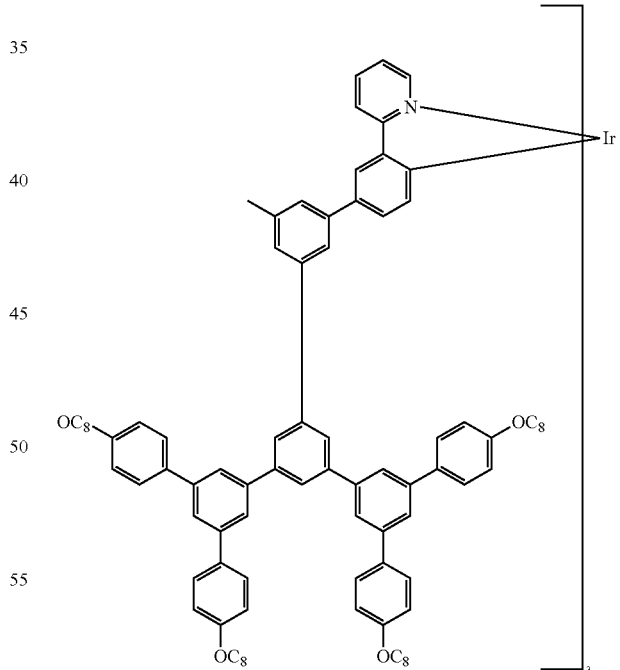

where $C_8$ is 2-ethylhexyl.

A further embodiment of the invention provides Rh or Ir complexes as shown in scheme 2 which simultaneously have ligands of the type present in compounds (I) and of the type present in compounds (II), i.e. mixed ligand systems. These are described by the formulae (Ia) and (IIa):

Scheme 2

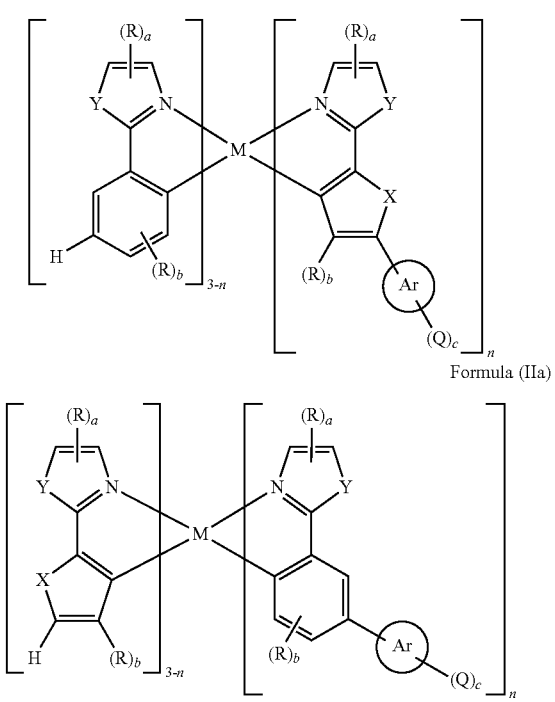

Formula (Ia)

Formula (IIa)

where the symbols and indices M, X, Y, R, Ar, Q, A⁻, $R^1$, $R^2$, $R^3$, $R^4$, a, b, c and n are as defined in claim 1.

Preference is given to compounds (I), (Ia), (II) and (IIa) according to the invention in which the symbol Y=O S.

Preference is likewise given to compounds (I), (Ia), (II) and (IIa) according to the invention in which Y=R—C=C—R, R—C=N—.

Preference is likewise given to compounds (I), (Ia), (II) and (IIa) according to the invention in which b=0.

Preference is likewise given to compounds (I), (Ia), (II) and (IIa) according to the invention in which Ar is an aryl group or Ar is a heteroaryl group.

Preference is likewise given to compounds (I), (Ia), (II) and (IIa) according to the invention in which the radical Ar is benzene, toluene, xylene, fluorobenzene, difluorobenzene, diphenyl, 1,2- or 1,3- or 1,4-terphenylene, tetraphenylene, naphthalene, fluorene, phenanthrene, anthracene, 1,3,5-triphenylbenzene, pyrene, perylene, chrysene, triptycene, [2.2] paracyclophane, pyridine, pyridazine, 4,5-benzo-pyridazine, pyrimidine, pyrazine, 1,3,5-triazine, pyrrole, indole, 1,2,5- or 1,3,4-oxa-diazole, 2,2'- or 4,4'-diazabiphenyl, quinoline, carbazole, 5,10H-dihydrophenazine, 10H-phenoxazine, phenothiazine, xanthene, 9-acridine, furan, benzofuran, thiophene or benzothiophene.

Particular preference is given to compounds (I), (Ia), (II) and (IIa) according to the invention in which Ar is carbazole, N-alkylcarbazole, N-alkylphenoxazine, pheno-thiazine and/ or xanthene, in particular phenyl, 1- or 2-naphthyl, 1-, 2- or 9-anthracenyl.

Preference is also given to unsymmetrically substituted aryl radicals Ar. In this context, unsymmetrical means that the aryl fragments including the substituents do not have a $C_2$ axis of symmetry which runs along the bond connecting the radical to the metal complex. The reason for this preference is that the solubility can be increased further in this way.

Preference is likewise given to compounds (I), (Ia), (II) and (IIa) according to the invention in which the radical Q is F, Cl, Br, CN, $NO_2$ $SiR_3$ or a straight-chain or branched or cyclic alkyl or alkoxy group which has from 1 to 6 carbon atoms and in which one or more adjacent $CH_2$ groups may be replaced by —$CF_2$—.

Furthermore, it is also possible for individual radicals Q to bear or be groups which can be crosslinked, e.g. by photochemical means. Such groups are disclosed, for example, in the patent application WO 02/10129.

Such substituents can be used when the corresponding complexes are applied as a pure layer and are to be modified by subsequent crosslinking before further processing steps.

Preference is likewise given to compounds (I), (Ia), (II) and (IIa) according to the invention in which M=Ir.

Preference is likewise given to compounds (I), (Ia), (II) and (IIa) according to the invention in which c is greater than or equal to 1.

The present invention also provides a process for preparing the compounds of the formulae (I) and (II) by reacting compounds of the formula (III) or (IV),

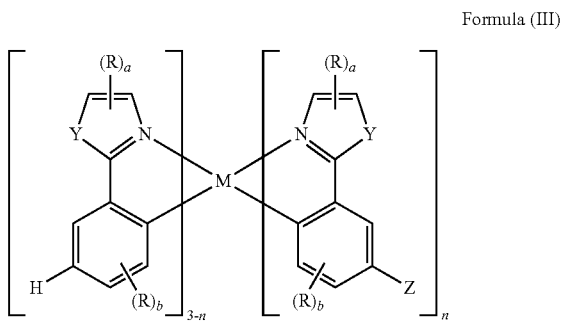

Formula (III)

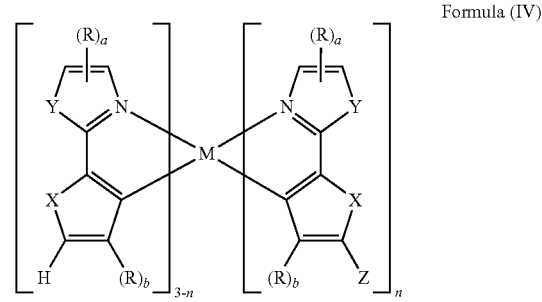

Formula (IV)

where the symbols and indices M, X, Y, R, a, b and n are as defined for the formulae (I) and (II), and Z is Cl, Br or I, with an arylboronic acid or an arylboronic ester of the formula (V)

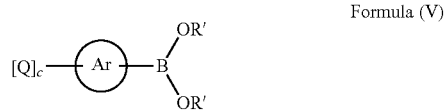

Formula (V)

where the symbols and indices Q, Ar and c are as defined in claim 1, and:

R' is identical or different on each occurrence and is H or an aliphatic or aromatic hydrocarbon radical having from 1 to 20 carbon atoms, where a plurality of substituents R' may form a monocyclic or polycyclic ring system, in a reaction medium and in the presence of a transition metal or a transition metal compound, a phosphorus-containing or nitrogen-containing additive and a base.

For the purposes of the present patent application, the term arylboronic acid encompasses the corresponding anhydrides (cyclic or open-chain).

Transition metals or transition metal compounds suitable for the purposes of the invention are nickel or nickel compounds and palladium or palladium compounds.

For the purposes of the invention, nickel and nickel compounds are, for example, elemental nickel, nickel sponge, nickel on kieselguhr, nickel on aluminum oxide, nickel on silica, nickel on carbon, nickel(II) acetate, nickel(II) acetylacetonate, nickel(II) chloride, bromide or iodide, addition compounds of the type $NiL_2X_2$ in which X is chlorine, bromine, iodine and L is an uncharged ligand such as ammonia, acetonitrile, propionitrile, benzonitrile, nickel(II) nitrate, nickel(II) sulfate, nickel(II) oxalate, biscyclooctadienenickel (0).

For the purposes of the invention, palladium and palladium compounds are, for example, elemental palladium, palladium sponge, palladium black, palladium on activated carbon, palladium on aluminum oxide, palladium on silica, palladium on alkali metal carbonates or alkaline earth metal carbonates, e.g. sodium carbonate, potassium carbonate, calcium carbonate, strontium carbonate or barium carbonate, palladium on strontium carbonate or barium sulfate, and palladium compounds such as palladium(II) acetate, palladium(II) trifluoroacetate, palladium(II) propionate, palladium(II) acetylacetonate, palladium(II) chloride, bromide or iodide, addition compounds of the type $PdL_2X_2$ in which X is chlorine, bromine, iodine and L is an uncharged ligand such as ammonia, acetonitrile, propionitrile, benzonitrile, cyclo-octadiene, palladium(II) nitrate, palladium(II) sulfate, tetramminepalladium(II) acetate, tetrakis(acetonitrile)palladium(II) tetrafluoroborate, tetrakis(triphenyl-phosphine)palladium(0) and tris(dibenzylideneacetone)dipalladium(0).

The molar ratio of nickel, a nickel compound, palladium or a palladium compound to the compounds (III) or (IV) is, according to the invention, from 0.1 n:1 to 0.00001 n:1.

According to the invention, a phosphine is used as phosphorus-containing additive.

Phosphine ligands suitable for the purposes of the invention are triarylphosphines, diarylalkylphosphines, aryldialkylphosphines, trialkylphosphines, trihetaryl-phosphines, dihetarylalkylphosphines, hetaryldialkylphosphines, diarylhetaryl-phosphines, aryldihetarylphosphines, where the substituents on the phosphorus can be identical or different, chiral or achiral, and one or more of the substituents can link the phosphorus groups of a plurality of phosphines and some of these linkages can also comprise one or more metal atoms, e.g. triphenylphosphine, tri-o-tolyl-phosphine, trimesitylphosphine, tri-o-anisylphosphine, tri-(2,4,6-trismethoxy-phenyl)phosphine, tert-butyl-di-o-tolylphosphine, di-tert-butyl-o-tolylphosphine, dicyclohexyl-2-biphenylphosphine, di-tert-butyl-2-biphenylphosphine, triethylphosphine, triisopropylphosphine, tricyclohexylphosphine, tri-tert-butylphosphine, tri-tert-pentylphosphine, bis(di-tert-butylphosphino)methane, 1,1'-bis(di-tert-butyl-phosphino)ferrocene.

Particular preference is given to the phosphines tri-o-tolylphosphine, dicyclohexyl-2-biphenylphosphine, di-tert-butyl-2-biphenylphosphine, tri-tert-butylphosphine and tri-tert-pentylphosphine.

According to the invention, imidazolium salts, imidazol-2-ylidenes or amines and aminocarboxylic acids are used as nitrogen-containing additives.

Preference is given to using imidazolium salts such as 1,3-bis(phenyl)imidazolium hydrochloride, 1,3-bis(2-methylphenyl)imidazolium hydrochloride, 1,3-bis(2,6-di-methylphenyl)imidazolium hydrochloride, 1,3-bis(2,4,6-trimethylphenyl)imidazolium hydrochloride, 1,3-bis(2,6-diisopropylphenyl)imidazolium hydrochloride, 1,3-bis(2,6-di-tert-butylphenyl)imidazolium hydrochloride or imidazol-2-ylidenes such as 1,3-bis-(phenyl)imidazol-2-ylidene, 1,3-bis(2-methylphenyl)imidazol-2-ylidene, 1,3-bis(2,6-dimethylphenyl)imidazol-2-ylidene, 1,3-bis(2,4,6-trimethylphenyl)imidazol-2-ylidene, 1,3-bis(2,6-diisopropylphenyl)imidazol-2-ylidene, 1,3-bis(2,6-di-tert-butylphenyl)-imidazol-2-ylidene, or aromatic amines and aminocarboxylic acids, e.g. pyridine, lutidine, 2,2'-bipyridyl or quinoline or α-, β-, γ, δ-aminocarboxylic acids or their N-alkylated forms or their sodium or potassium salts, e.g. anthranilic acid, dimethyl-anthranilic acid, 2-pyridinecarboxylic acid, dimethylglycine, dimethylaminobutyric acid or 3-indolylacetic acid, as nitrogen-containing additives.

The molar ratio of the phosphorus- or nitrogen-containing additive to nickel, a nickel compound, palladium or a palladium compound is, according to the invention, from 0.5:1 to 1000:1.

Bases suitable for the purposes of the invention are organic bases such as alkali metal alkoxides and alkaline earth metal alkoxides, e.g. lithium, sodium, potassium, magnesium, strontium and barium methoxide, ethoxide, propoxide, butoxide, isopropoxide, isobutoxide, sec-butoxide, tert-butoxide, phenoxide, organic amines such as trimethylamine, triethylamine, tributylamine, diisopropylamine, N-ethyldiiso-propylamine, morpholine, N-methylmorpholine, N-ethylmorpholine, pyridine, 2-, 3-, 4-methylpyridine, lutidine or collidine, tetraalkylammonium hydroxides such as tetramethylammonium, tetraethylammonium, tetrapropylammonium and tetrabutylammonium hydroxides, alkali metal carboxylates and alkaline earth metal carboxylates, e.g. lithium, sodium, potassium, magnesium, strontium and barium formate, acetate, propionate, butyrate, oxalate or benzoate, or mixtures of the bases mentioned.

Further bases which are suitable for the purpose of the invention are inorganic bases such as ammonium, alkali metal oxides and alkaline earth metal oxides, e.g. lithium, sodium, potassium, magnesium, strontium and barium oxides, alkali metal hydroxides and alkaline earth metal hydroxides, e.g. lithium, sodium, potassium, magnesium, strontium and barium hydroxides, alkali metal carbonates and alkaline earth metal carbonates, e.g. lithium, sodium, potassium, cesium, magnesium, strontium and barium carbonates, alkali metal hydrogencarbonates, e.g. lithium, sodium, potassium, cesium hydrogencarbonate, alkali metal phosphates, hydrogen-phosphates, dihydrogenphosphates, e.g. lithium, sodium, potassium phosphate, hydrogenphosphate, dihydrogenphosphate, alkali metal fluorides and alkaline earth metal fluorides, e.g. lithium, sodium, potassium, cesium, magnesium, strontium and barium fluorides, or mixtures of the bases mentioned.

The molar ratio of the organic or inorganic base to the compounds (III) or (IV) is, according to the invention, from 0.5 n:1 to 100 n:1.

Reaction media suitable for the purposes of the invention are protic or aprotic, halogen-free or halogenated solvents, e.g. alcohols such as methanol, ethanol, propanol, butanol, polyhydric alcohols such as ethylene glycol or propylene glycol, nitriles such as acetonitrile, propionitrile or benzonitrile, ethers such as diethyl ether, THF or dioxane, aromatic hydrocarbons such as toluene, o-, m-, p-xylene or a mixture of the isomeric xylenes, mesitylene, anisole, nitrobenzene or chlorobenzene, N,N-dialkylamides such as dimethylformamide, dimethylacetamide or N-methyl-pyrrolidinone, sulfoxides such as dimethyl sulfoxide, sulfones such as dimethyl sulfone or sulfolane, or mixtures of the solvents mentioned.

If desired, water can be added to the organic reaction medium, in which case, depending on the organic solvent used, the reaction can be carried out in a single phase or in a two-phase mixture.

According to the invention, the reaction is carried out in the temperature range from 20° C. to 200° C., preferably from 60° C. to 150° C.

According to the invention, the concentration of the rhodium-containing or iridium-containing starting materials, viz. compounds (III) or compounds (IV), is in the range from 0.0005 mol/l to 2 mol/l, particularly preferably in the range from 0.002 mol/l to 0.5 mol/l.

According to the invention, the rhodium-containing or iridium-containing starting materials can be present as a solution or suspension in the reaction medium.

According to the invention, the reaction is carried out over a period of from 1 hour to 100 hours, preferably over a period of from 1 hour to 60 hours.

According to the invention, the reaction can be carried out with addition of inert milling media, e.g. ceramic, glass or metal spheres or Pall or Raschig rings.

The preparation of the compounds of the formulae (I), (Ia), (IIa) and (II) according to the invention is carried out by means of the above-described process and leads to compounds having a purity (determined by means of $^1$H-NMR and/or HPLC) of more than 99%.

The synthetic methods described here allow, inter alia, the examples of compounds (I), (Ia), (IIa) or (II) shown below to be prepared.

Example 1

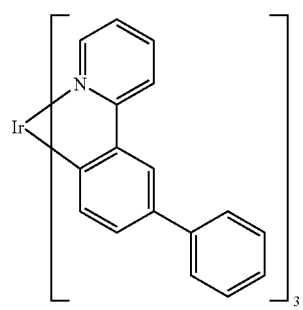

Example 2

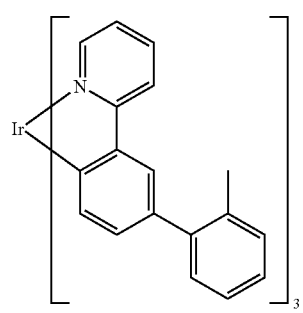

-continued

Example 3

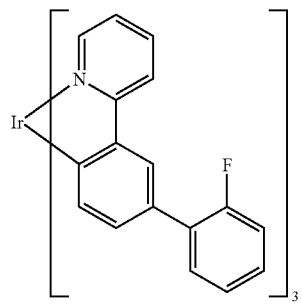

Example 4

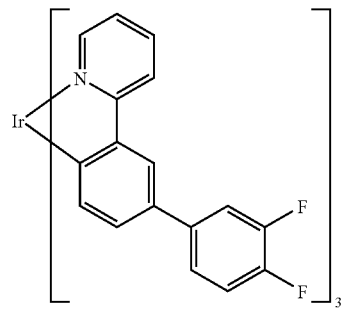

Example 5

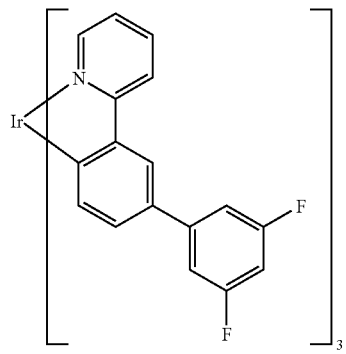

Example 6

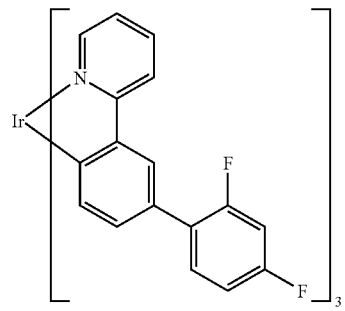

Example 7

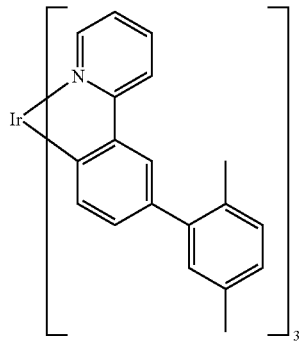

Example 8
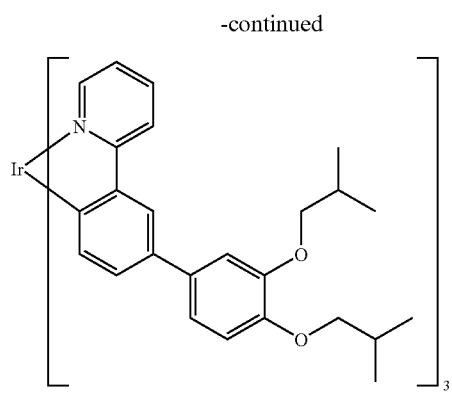
Example 9
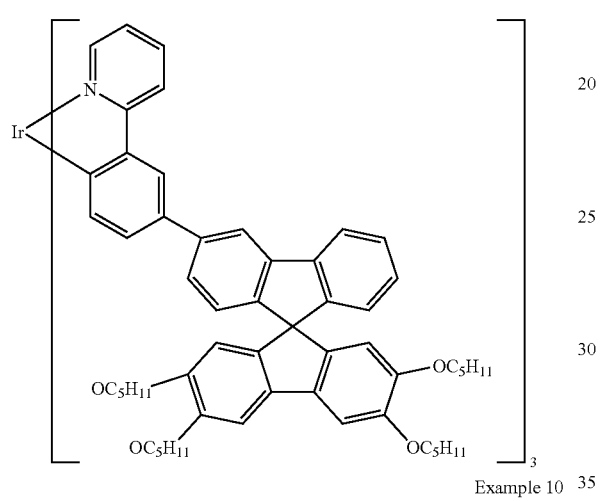
Example 10
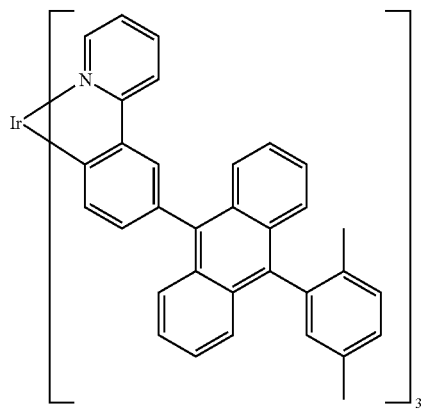
Example 11
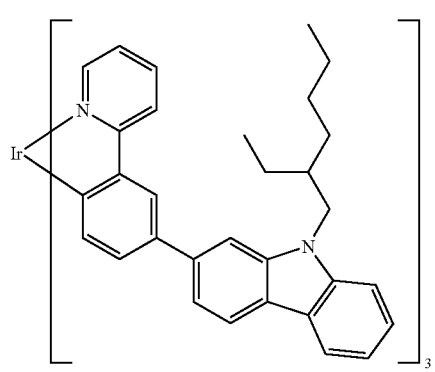
Example 12
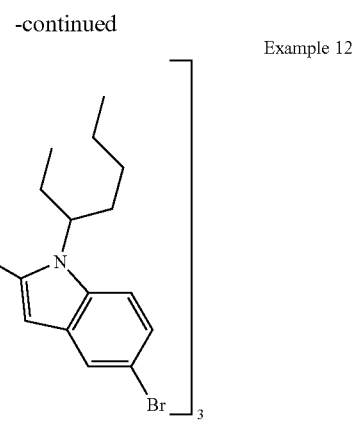
Example 13
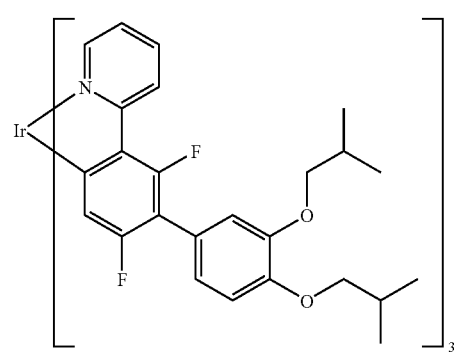
Example 14
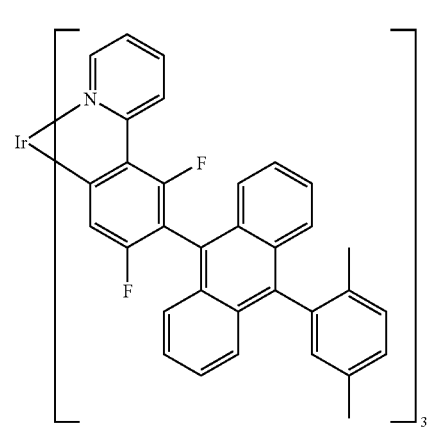
Example 15
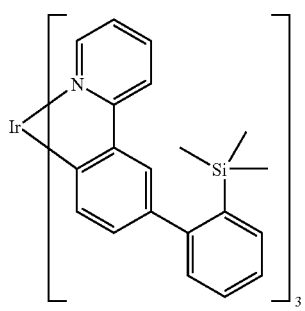

-continued
Example 16
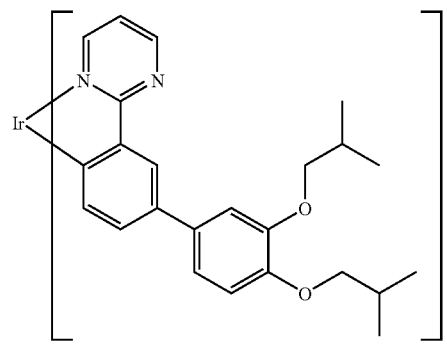
Example 17
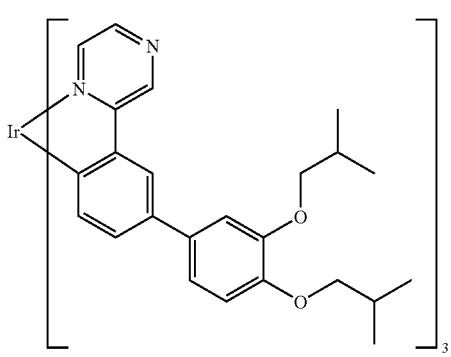
Example 18
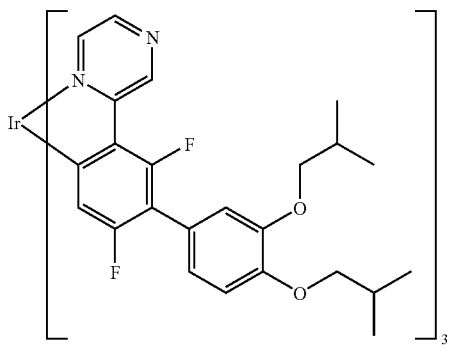
Example 19
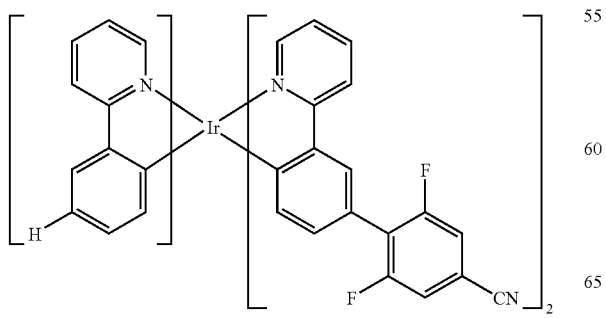
-continued
Example 20
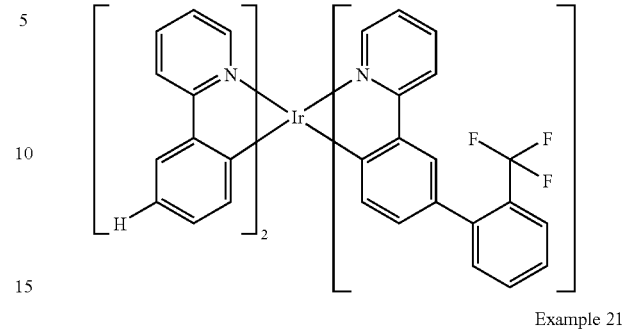
Example 21
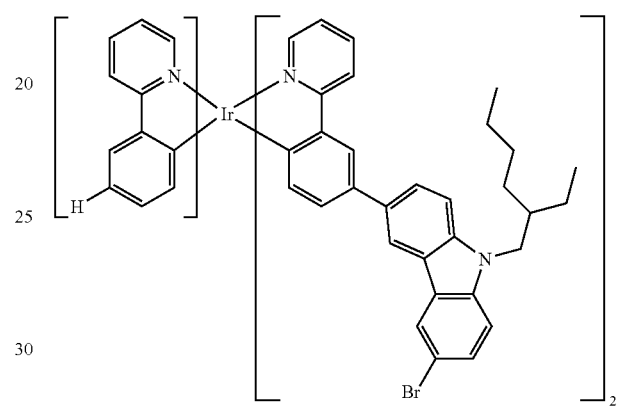
Example 22
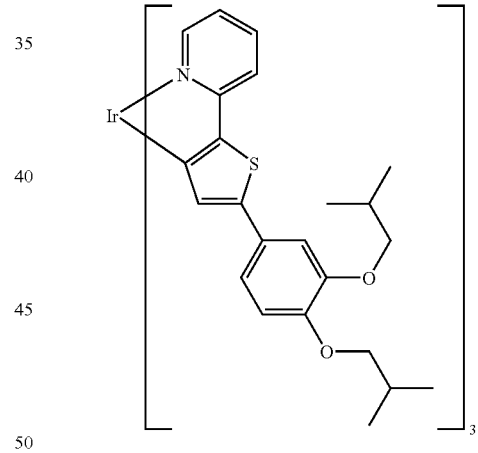
Example 23
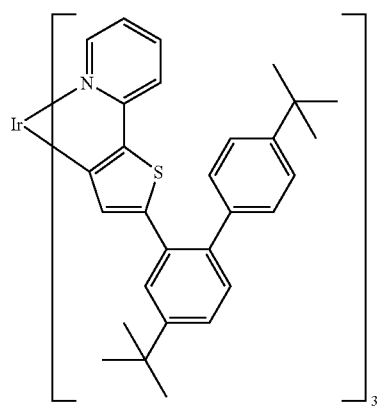

-continued
Example 24
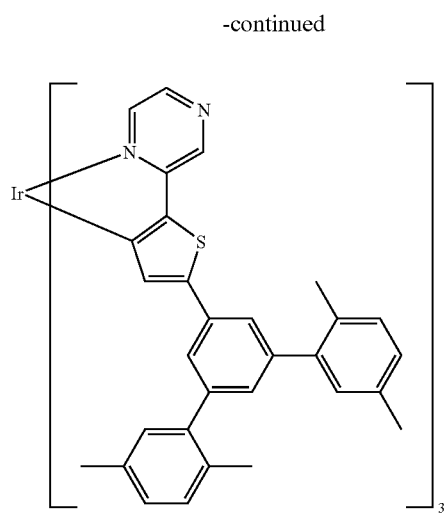
Example 25
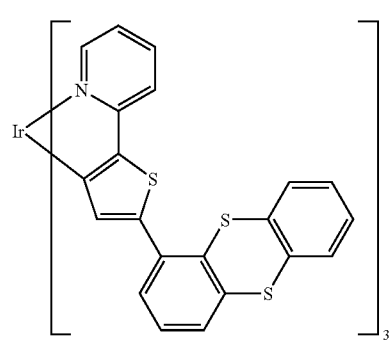
Example 26
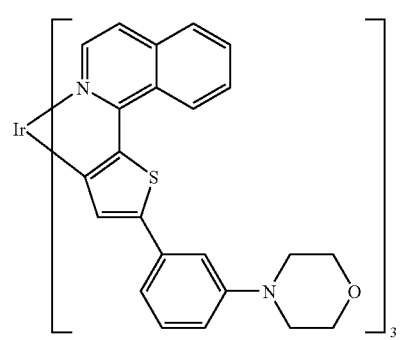
Example 27
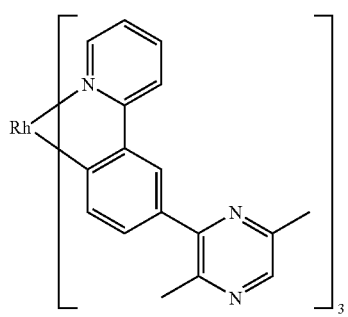
-continued
Example 28
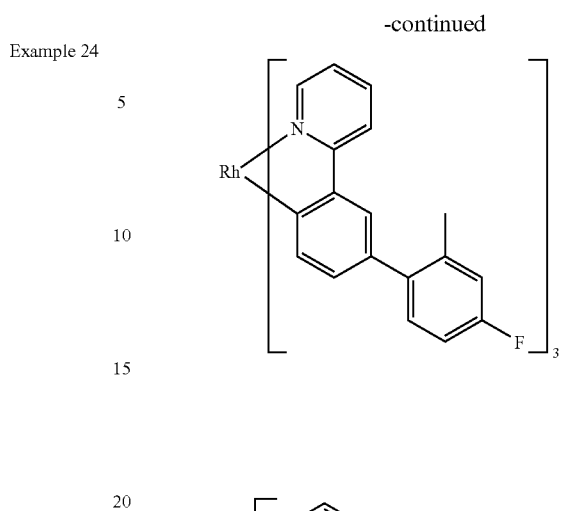
Example 29
Example 30
Example 31
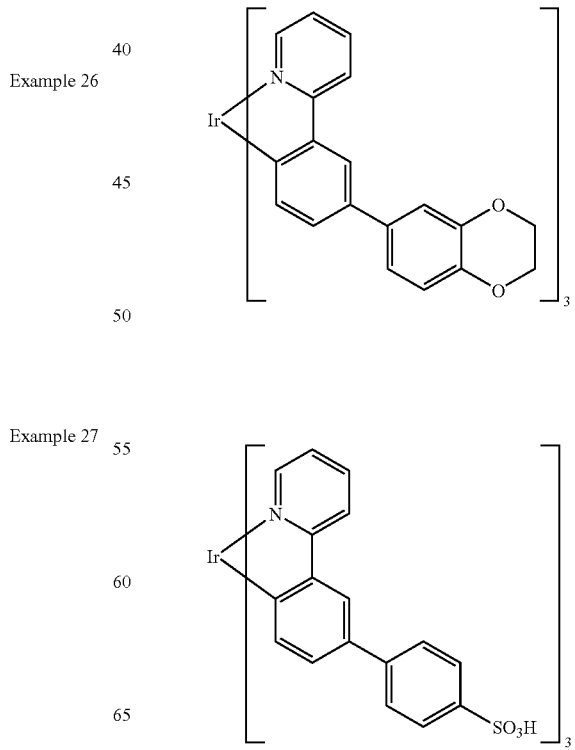

-continued

Example 32

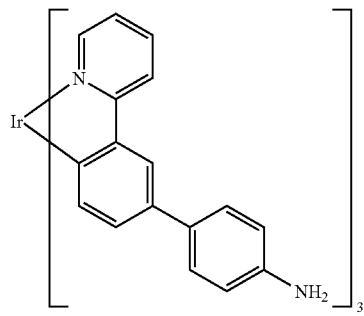

Example 33

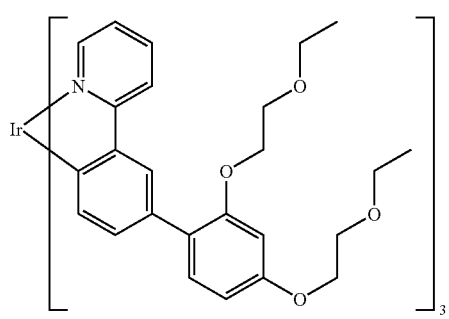

Example 34

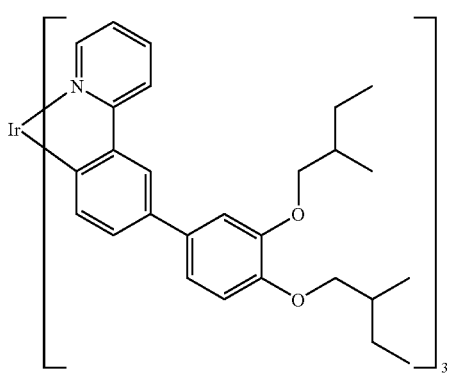

Example 35

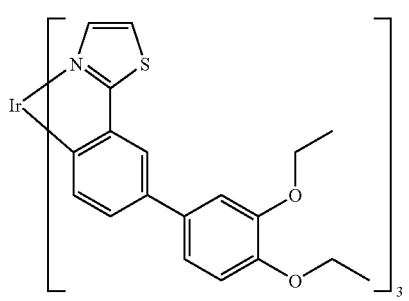

-continued

Example 36

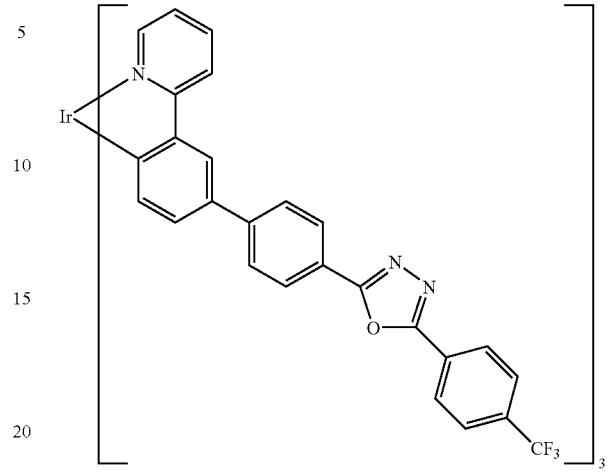

When using the materials according to the invention in the electronic components mentioned above and also those mentioned below, it can be advantageous to mix them into further materials.

Particular preference is in this case given to mixing into polymeric compounds.

The present invention therefore further provides mixtures of one or more compounds of the formula (I/Ia), and/or (II/IIa) as claimed in claims 1 and 2 with unconjugated, partially conjugated or conjugated polymers.

Examples of such polymers which are suitable for mixing are polymers from the group consisting of polyfluorenes, polyspirobifluorenes, poly-para-phenylenes, poly-para-phenylene-vinylenes, polycarbazoles, polyvinylcarbazoles, polythiophenes and copolymers comprising a plurality of the units mentioned here.

Since coating is preferably carried out from solution, it is preferred that the corresponding polymers are soluble in organic solvents.

It is also possible to mix the materials according to the invention with nonpolymeric materials. Furthermore, it can also be advantageous to use multicomponent mixtures comprising materials according to the invention, polymers and further low molecular weight materials.

A further possibility is to polymerize the compounds according to the invention obtained in this way, e.g. compounds as described in examples 12 and 21, as comonomers into conjugated or partially conjugated polymers. Thus, they can be incorporated by polymerization into soluble polyfluorenes (e.g. as described in EP-A-842208 or WO 00/22026), polyspirobifluorenes (e.g. as described in EP-A-707020), poly-para-phenylenes (e.g. as described in WO 92/18552), polycarbazoles, polythiophenes (e.g. as described in EP-A-1028136) or copolymers comprising a plurality of the units mentioned here.

These polymers are used as active components in electronic components such as organic light-emitting diodes (OLEDs), organic integrated circuits (O-ICs), organic field effect transistors (OFETs), organic thin film transistors (OTFTs), organic solar cells (O-SCs) or organic laser diodes (O-lasers).

The polyfluorenes disclosed in EP-A-842208 and WO 00/22026 are hereby incorporated by reference into the present description.

The polyspirobifluorenes disclosed in EP-A-707020 are hereby incorporated by reference into the present description.

The poly-para-phenylenes disclosed in WO 92/18552 are hereby incorporated by reference into the present description.

The polythiophenes disclosed in EP-A-1028136 are hereby incorporated by reference into the present description.

The present invention is illustrated by the following examples without being restricted thereto. A person skilled in the art will be able to prepare further complexes according to the invention or apply the process of the invention on the basis of the information given, without needing to make an inventive step.

EXAMPLES

1. Synthesis of Symmetrically and Unsymmetrically Functionalized Tris-Ortho-Metallated Organorhodium Organoiridium Compounds The following syntheses were, unless indicated otherwise, carried out in solvents dried under a protective gas atmosphere. The starting materials were procured from ALDRICH [benzeneboronic acid, 2-methylbenzeneboronic acid, 2-fluorobenzene-boronic acid, 2,4-difluorobenzeneboronic acid, 3,4-difluorobenzeneboronic acids 3,5-difluorobenzeneboronic acid, 2,5-dimethylphenylboronic acid, anhydrous potassium phosphate, palladium(II) acetate, tri-o-tolylphosphine]. 3,4-Bisbutoxy-benzeneboronic acid was prepared as described in the published patent application WO 01/34722 A1, and fac-Tris[2-(2-pyridinyl-κN)(5-bromophenyl)-κC] iridium(III) was prepared as described in WO 02/068435.

Example 1 fac-Tris[2-(2-pyridinyl-κN)(5-(phenyl)phenyl)-κC] iridium(III)

A mixture of 8.92 g (10 mmol) of fac-Tris[2-(2-pyridinyl-κN)(5-bromophenyl)-κC]) iridium(III), 5.12 g (42 mmol) of benzeneboronic acid and 13.37 g (63 mmol) of tri-potassium phosphate (anhydrous) was admixed with a solution of 182.62 mg (0.6 mmol) of tri-o-tolylphosphine in 160 ml of dioxane and a solution of 22.44 mg (0.1 mmol) of palladium (II) acetate in 160 ml of toluene and 150 ml of water. The reaction mixture was heated at 85° C. for 60 hours while stirring well by means of a precision glass stirrer. After cooling, the mixture was washed twice with 200 ml each time of water. The phases were separated and the organic phase was evaporated to 50 ml. The solution was subsequently poured into 150 ml of ethanol. The yellow, microcrystalline precipitate obtained in this way was filtered off (P4) and washed three times with 100 ml each time of ethanol and then dried under reduced pressure (60° C., $10^{-4}$ mbar). The yield, as a purity of >99.0% as determined by $^1$H-NMR and HPLC, was 8.31-8.54 g, corresponding to 94.2-96.8%.

$^1$H-NMR (DMSO): [ppm]=8.39-8.38 (br. m, 3H), 8.10 (d, 3H), 7.87-7.84 (br. m, 3H), 7.71-7.69 (br m, 6H), 7.56-7.55 (br. m, 3H), 7.41-7.38 (br. m, 6H), 7.27-7.24 (m, 3H), 7.20-7.18 (m, 3H), 7.10-7.08 (m, 3H), 6.86-6.85 (m, 3H).

Example 2 fac-tris[2-(2-pyridinyl-κN)(5-(o-tolyl)phenyl)-κC] iridium(III)

A mixture of 8.92 g (10 mmol) of fac-Tris[2-(2-pyridinyl-κN)(5-bromophenyl)-κC]-iridium(III), 8.56 g (63 mmol) of 2-methylbenzeneboronic acid and 13.37 g (63 mmol) of tri-potassium phosphate (anhydrous) was admixed with a solution of 182.62 mg (0.6 mmol) of tri-o-tolylphosphine in 160 ml of dioxane and a solution of 22.44 mg (0.1 mmol) of palladium(II) acetate in 160 ml of toluene and 150 ml of water. The reaction mixture was heated at 85° C. for 60 hours while stirring well by means of a precision glass stirrer. Work-up analogous to example 1. The yield, at a purity of >99.0% as determined by $^1$H-NMR and HPLC, was 8.66-8.84 g, corresponding to 93.7-95.4%.

$^1$H-NMR (DMSO): [ppm]=8.26-8.24 (br. m, 3H), 7.83-7.79 (br. m, 3H), 7.76-7.75 (m, 3H), 7.58-7.57 (m, 3H), 7.25-7.17 (br. m, 15H), 6.84-6.82 m, 3H), 6.76-6.74 (m, 3H), 2.27 (s, 9H).

Example 3 fac-Tris[2-(2-pyridinyl-κN)(5-(2-fluorophenyl)phenyl)-κC]iridium(III)

A mixture of 8.92 g (10 mmol) of fac-Tris[2-(2-pyridinyl-κN)(5-bromophenyl)-κC]-iridium(III), 5.87 g (42 mmol) of 2-fluorobenzeneboronic acid and 13.37 g (63 mmol) of tripotassium phosphate (anhydrous) was admixed with a solution of 182.62 mg (0.6 mmol) of tri-o-tolylphosphine in 160 ml of dioxane and a solution of 22.44 mg (0.1 mmol) of palladium(II) acetate in 160 ml of toluene and 150 ml of water. The reaction mixture was heated at 85° C. for 60 hours while stirring well by means of a precision glass stirrer. Work-up analogous to example 1. The yield, at a purity of >99.0% as determined by $^1$H-NMR and HPLC, was 9.04-9.16 g, corresponding to 96.5-97.8%.

$^1$H-NMR (DMSO): [ppm]=8.28-8.27 (br. m, 3H), 7.97 (br s, 3H), 7.87-7.83 (br. m, 3H), 7.59-7.54 (br. m, 6H), 7.33-7.30 (br. m, 3H), 7.25-7.20 (br. m, 9H), 6.98-6.96 (m, 3H), 6.87-6.86 (m, 3H).

Example 4 fac-Tris[2-(2-pyridinyl-κN)(5-(3,4-difluorophenyl) phenyl)-κC]-iridium(III)

A mixture of 8.92 g (10 mmol) of fac-Tris[2-(2-pyridinyl-κN)(5-bromophenyl)-κC]-iridium(III), 6.63 g (42 mmol) of 3,4-difluorobenzeneboronic acid and 13.37 g (63 mmol) of tripotassium phosphate (anhydrous) was admixed with a solution of 182.62 mg (0.6 mmol) of tri-o-tolylphosphine in 160 ml of dioxane and a solution of 22.44 mg (0.1 mmol) of palladium(II) acetate in 160 ml of toluene and 150 ml of water. The reaction mixture was heated at 85° C. for 60 hours while stirring well by means of a precision glass stirrer. Work-up analogous to example 1. The yield, at a purity of >99.0% as determined by $^1$H-NMR and HPLC, was 9.16-9.47 g, corresponding to 92.5-95.6%.

$^1$H-NMR (DMSO): [ppm]=8.45-8.43 (br. m, 3H), 8.14 (br s, 3H), 7.89-7.86 (br. m, 3H), 7.85-7.79 (br. m, 3H), 7.56-7.55 (m, 6H), 7.45-7.40 (br. m, 3H), 7.21-7.19 (br. m, 3H), 7.10-7.08 (br. m, 3H), 6.82-6.81 (m, 3H).

Example 5 fac-Tris[2-(2-pyridinyl-κN)(5-(3,5-difluorophenyl) phenyl)-κC]-iridium(III)

A mixture of 8.92 g (10 mmol) of fac-Tris[2-(2-pyridinyl-κN)(5-bromophenyl)-κC]-iridium(III), 6.63 g (42 mmol) of 3,5-difluorobenzeneboronic acid and 13.37 g (63 mmol) of tripotassium phosphate (anhydrous) was admixed with a solution of 182.62 mg (0.6 mmol) of tri-o-tolylphosphine in 160 ml of dioxane and a solution of 22.44 mg (0.1 mmol) of palladium(II) acetate in 160 ml of toluene and 150 ml of water. The reaction mixture was heated at 85° C. for 60 hours while stirring well by means of a precision glass stirrer. Work-up analogous to example 1. The yield, at a purity of >99.0% as determined by $^1$H-NMR and HPLC, was 9.64-9.75 g, corresponding to 97.3-98.4%.

$^1$H-NMR (DMSO): [ppm]=8.50-8.48 (br. m, 3H), 8.21-8.20 (br. d, 3H), 7.90-7.87 (br. m, 3H), 7.55-7.54 (m, 3H), 7.51-7.49 (br. m, 6H), 7.25-7.21 (br. m, 3H), 7.18-7.14 (m, 3H), 7.09-7.05 (br. m, 3H), 6.83-6.80 (m, 3H).

Example 6 fac-Tris[2-(2-pyridinyl-κN)(5-(2,4-difluorophenyl) phenyl)-κC]-iridium(III)

A mixture of 8.92 g (10 mmol) of fac-Tris[2-(2-pyridinyl-κN)(5-bromophenyl)-κC]-iridium(III), 6.63 g (42 mmol) of 2,4-difluorobenzeneboronic acid and 13.37 g (63 mmol) of tripotassium phosphate (anhydrous) was admixed with a solution of 182.62 mg (0.6 mmol) of tri-o-tolylphosphine in 160 ml of dioxane and a solution of 22.44 mg (0.1 mmol) of palladium(II) acetate in 160 ml of toluene and 150 ml of water. The reaction mixture was heated at 85° C. for 60 hours while stirring well by means of a precision glass stirrer. Work-up analogous to example 1. The yield, at a purity of >99.0% as determined by $^1$H-NMR and HPLC, was 9.45-9.59 g, corresponding to 95.4-96.8%.

$^1$H-NMR (DMSO): [ppm]=8.29-8.27 (br. m, 3H), 7.95 (br s, 3H), 7.87-7.83 (br. m, 3H), 7.63-7.59 (br m, 3H), 7.55-7.54 (br. m, 3H), 7.30-7.23 (br. m, 3H), 7.22-7.20 (m, 3H), 7.14-7.11 (br. m, 3H), 6.94-6.92 (br. m, 3H), 6.85-6.84 (m, 3H)

Example 7 fac-Tris[2-(2-pyridinyl-κN)(5-(2,5-dimethylphenyl) phenyl)-κC]-iridium(III)

A mixture of 8.92 g (10 mmol) of fac-Tris[2-(2-pyridinyl-κN)(5-bromophenyl)-κC]-iridium(III), 9.29 g (62 mmol) of 2,5-dimethylbenzeneboronic acid and 13.37 g (63 mmol) of tripotassium phosphate (anhydrous) was admixed with a solution of 182.62 mg (0.6 mmol) of tri-o-tolylphosphine in 160 ml of dioxane and a solution of 22.44 mg (0.1 mmol) of palladium(II) acetate in 160 ml of toluene and 150 ml of water. The reaction mixture was heated at 85° C. for 48 hours while stirring well by means of a precision glass stirrer. Work-up analogous to example 1. The yield, at a purity of >99.0% as determined by $^1$H-NMR and HPLC, was 9.24-9.33 g, corresponding to 95.6-96.5%.

$^1$H-NMR (DMSO): [ppm]=8.49-8.23 (br. m, 3H), 7.82-7.78 (br. m, 3H), 7.74-7.73 (m, 3H), 7.57-7.56 (m, 3H), 7.19-7.17 (br. m, 3H), 7.12-7.11 (m, 3H), 7.05 (br s, 3H), 7.00-6.98 (br. m, 3H), 6.82-6.81 (d, 3H), 6.75-6.73 (br. m, 3H), 2.26 (s, 9H), 2.22 (s, 9H).

Example 8 fac-Tris[2-(2-pyridinyl-κN)(5-(3,4-bis(2-methylpropoxy)phenyl) phenyl)-κC]iridium(III)

A mixture of 8.92 g (10 mmol) of fac-Tris[2-(2-pyridinyl-κN)(5-bromophenyl)-κC]-iridium(III), 19.9 g (75 mmol) of 3,4-bis(2-methylpropoxy)phenylboronic acid and 13.37 g (63 mmol) of tripotassium phosphate (anhydrous) was admixed with a solution of 182.62 mg (0.6 mmol) of tri-o-tolylphosphine in 160 ml of dioxane and a solution of 22.44 mg (0.1 mmol) of palladium(II) acetate in 160 ml of toluene and 150 ml of water. The reaction mixture was heated at 85° C. for 48 hours while stirring well by means of a precision glass stirrer. Work-up analogous to example 1. The yield, at a purity of >99.0% as determined by $^1$H-NMR and HPLC, was 12.03-12.44 g, corresponding to 91.5-94.6%.

$^1$H-NMR (DMSO): [ppm]=8.37-8.35 (br. m, 3H), 8.00 (br d, 3H), 7.86-7.82 (br. m, 3H), 7.56-7.55 (m, 3H), 7.21-7.20 (m, 3H), 7.16-7.14 (br. m, 6H), 7.02-7.00 (m, 3H), 6.95-6.93 (m, 3H), 6.82-6.80 (m, 3H), 3.82 (d, 6H), 3.74 (d, 6H), 2.01 (m, 6H), 1.00-0.98 (m, 36H).

Example 9 fac-Tris[2-(2-pyridinyl-κN)(5-(2', 3',6',7'-tetrakis(2-methylbutoxy)-9,9'-spirobifluorenyl)phenyl)-κC] iridium(III)

A mixture of 8.92 g (10 mmol) of fac-Tris[2-(2-pyridinyl-κN)(5-bromophenyl)-κC]-iridium(III), 30.0 g (42 mmol) of 2',3',6',7'-tetrakis(2-methylbutoxy)-9,9'-spirobi-fluorenyl-2-boronic acid and 13.37 g (63 mmol) of tripotassium phosphate (anhydrous) was admixed with a solution of 182.62 mg (0.6 mmol) of tri-o-tolylphosphine in 160 ml of dioxane and a solution of 22.44 mg (0.1 mmol) of palladium(II) acetate in 160 ml of toluene and 150 ml of water. The reaction mixture was heated at 85° C. for 48-hours while stirring well by means of a precision glass stirrer. Work-up analogous to example 1. The yield, at a purity of >99.8% as determined by $^1$H-NMR, was 23.7 g, corresponding to 93.1%.

$^1$H-NMR (DMSO): [ppm]=7.85 (d, 3H), 7.837.78 (m, 6H), 7.63 (s, 3H), 7.56-7.52 (m, 6H), 7.41-7.40 (d, 3H), 7.33-7.30 (m, 3H), 7.21 (d, 6H), 7.06 (m, 3H), 6.92-6.90 (br, d, 6H), 6.80 (m, 3H), 6.70-6.53 (s br, 3H), 6.64 (d, 3H), 6.16 (d, 6H), 3.85 (m, 6H), 3.83 (m, 6H), 3.40 (m, 12H), 1.92 (m, 6H), 1.68 (m, 12H), 1.44-1.36 (m, 6H), 1.33-1.27 (m, 6H), 1.13-1.07 (m, 6H), 1.05-1.03 (m, 18H), 0.97-0.94 (m, 18H), 0.86-0.82 (m, 18H), 0.81-0.76 (m, 18H).

2. Data on the Solubility of Complexes

TABLE 1

Solubilities of various complexes according to the invention.

| Compound | Aryl radical | Stability @ 20° C. in toluene, [g/l] | Comment |
|---|---|---|---|
| Ir(ppy)$_3$ | None | <0.30 | Comparative example |
| 1 | Phenyl | 6.3 | According to the invention |
| 2 | o-Tolyl | 25 | According to the invention |
| 7 | 2,5-Dimethylphenyl | 32 | According to the invention |
| 8 | 3,4-Bis(2-methylpropoxy)-phenyl | 92 | According to the invention |
| 34 | Bis-3,4-(2-methylbutoxy-phenyl | 126 | According to the invention |

As can easily be seen from the data, merely the introduction of a phenyl group on the ligand (change from the comparative compound Ir(ppy)$_3$ to compound 1) increases the solubility by a factor of 20. A further increase can, as indicated above, then be achieved by appropriate substitution on the aryl radical.

3. Production and Characterization of Organic Electroluminescence Devices Comprising Compounds According to the Invention LEDs were produced by the general method outlined below. This naturally had to be adapted in each individual case to the individual circumstances (e.g. layer thickness variation to achieve optimal efficiency or color).

3.1 General Method of Producing OLEDs

After the ITO-coated substrate (e.g. glass supports, PET film) have been cut to the correct size, they are cleaned in a number of cleaning steps in an ultrasonic bath (e.g. soap solution, Millipore water, isopropanol).

To dry the substrates, they are blown with an $N_2$ gun and stored in a desiccator. Before coating with the organic films, they are treated by means of an ozone plasma apparatus for about 20 minutes. It can be advisable to use a polymeric hole injection layer as first organic layer. This is generally a conjugated, conductive polymer, e.g. a polyaniline derivative (PANI) or a polythiophene derivative (e.g. PEDOT, BAYTRON P™ from H.C. Starck). This is then applied by spin coating.

The organic layer(s) can be applied by various methods:
1. To produce the hybrid structures mentioned in the text, the triplet emitters can be applied as a pure layer or as a mixture with other compounds from solution (e.g. by spin coating).
2. However, it can likewise be possible to apply some of the compounds according to the invention by normal vacuum processing. Appropriate processes have been documented many times, for example in the as yet unpublished patent application DE 10215010.9.

The following OLEDs were produced and characterized. It should be pointed out that the respective devices are generally not optimized (i.e., for example, the layer thicknesses or the precise compositions were not varied).

3.2 LED Examples of Type 1 (hybrid OLEDs):

The OLEDs shown in table 1 were prepared from solution and examined. The individual results are summarized in the table below.

The following further compounds were employed:
PEDOT=conductive polythiophene derivative (PEDOT=poly((2,3-ethylene-dioxy)thiophene); applied from aqueous dispersion, containing PSSH (polystyrenesulfonic acid); commercially available as BAYTRON B from BAYER AG, Leverkusen.

PVK=polyvinylcarbazole, procured from ALDRICH.

S-CBP=2,2',7,7'-tetrakis(9-carbazolyl)spiro-9,9'-bifluorene; synthesized from 2,2',7,7'-tetrabromospiro-9,9'-bifluorene and carbazole as described in the unpublished patent application DE 10153450.7.

TABLE 2

Device data for OLEDs comprising complexes according to the invention.

| # | PEDOT [nm] | Org. layer [nm] | Comp. from example | Composition of Org. layer | Coating from | Eff. [Cd/A]/ U [V] @ 100 Cd/m² | Eff. [Cd/A]/ U [V] @ 800 Cd/m² | Eff. [Cd/A]/ U [V] @ 5000 Cd/m² | $\lambda_{max}$ (EL) [nm] (CIE 1931) |
|---|---|---|---|---|---|---|---|---|---|
| 1 | 20 | 80 | 1 | PVK:S-CBP:1 80:18:2 | Chlorobenzene 20 mg/ml | 11.6/11 | 17.4/13 | 22.2/15 | 525 (0.36/0.60) |
| 2 | 20 | 80 | 7 | PVK:S-CBP:7 80:18:2 | Chlorobenzene 20 mg/ml | 14.8/10 | 18.4/11 | 19.5/13 | 522 (0.37/0.59) |
| 3 | 20 | 80 | 8 | PVK:S-CBP:8 80:18:2 | Chlorobenzene 20 mg/ml | 20.8/11 | 24.3/13 | 24.4/15 | 530 (0.39/0.59) |

The efficiencies achieved by these unoptimized LEDs, particularly as high luminances, are surprisingly high. What must certainly still be able to be achieved by optimization (e.g. better injection conditions) is a significant reduction in the voltages required.

The invention claimed is:
1. A compound of the formula (I),
Scheme 1

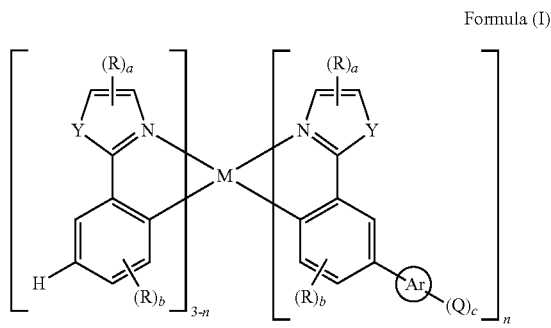

Formula (I)

where the symbols and indices have the following meanings:

M is Rh or Ir;
X is O, S or Se;
Y is S, O, R—C=C—R or R—C=N;
R is identical or different on each occurrence and is H, F, Cl, $NO_2$, CN, a straight-chain or branched or cyclic alkyl or alkoxy group which has from 1 to 20 carbon atoms and in which one or more nonadjacent $CH_2$ groups is optionally replaced by —O—, —S—, —$NR^1$— or —$CONR^2$— and one or more H atoms is optionally replaced by F, or an aryl or heteroaryl group which has from 4 to 14 carbon atoms and is optionally substituted by one or more, nonaromatic radicals R;
Ar is benzene, toluene, xylene, fluorobenzene, difluorobenzene, diphenyl, tetraphenylene, naphthalene, fluorene, phenanthrene, anthracene, 1,3,5-triphenylbenzene, pyrene, perylene, chrysene, triptycene, [2.2]paracyclophane, pyridine, pyridazine, 4,5-benzopyridazine, pyrimidine, pyrazine, 1,3,5-triazine, pyrrole, indole, 1,2,5- or 1,3,4-oxadiazole, 2,2'- or 4,4'-diazabiphenyl, quinoline, N-alkylcarbazole, 5,10H-dihydrophenazine, 10H-phenoxazine, N—alkylphenoxazine, phenothiazine, xanthene, 9-acridine, furan, benzofuran, thiophene or benzothiophene;

Q is identical or different on each occurrence and is F, Cl, Br, I, CN, COOH, $NH_2$, OH, SH, $NO_2$, $SO_3H$, $SiR_3$ or a straight-chain or branched or cyclic alkyl or alkoxy group which has from 1 to 20 carbon atoms and in which one or more nonadjacent $CH_2$ groups is optionally replaced by —O—, —S—, —CO—, —COO—, —O—CO—, —$NR^1$—, —$(NR^2R^3)^+A^-$ or —$CONR^4$— and one or more H atoms is optionally replaced by F, or heteroaryl group which has from 4 to 14 carbon atoms and is optionally substituted by one or more, nonaromatic radicals R;

$A^-$ is a singly charged anion or its equivalent;

are identical or different and are each H or an aliphatic or aromatic hydrocarbon radical having from 1 to 20 carbon atoms;

a is 0, 1, 2, 3 or 4, b is 0, 1, 2 or 3, c is from 0 to 15;

n is 1, 2 or 3;

with the exception of the compounds:

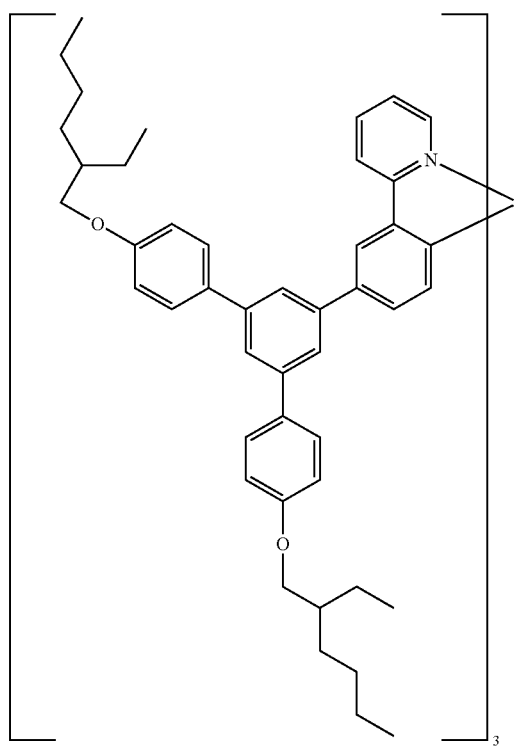

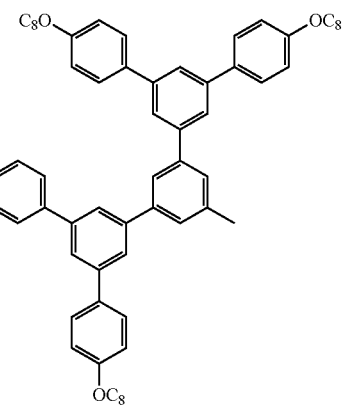

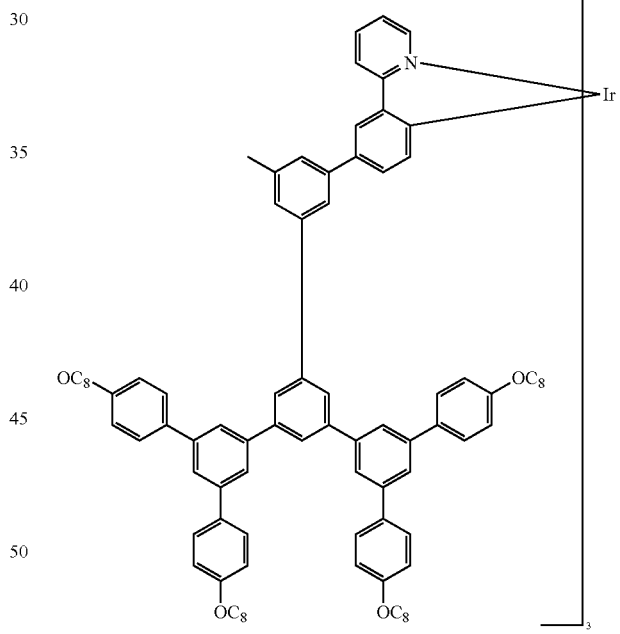

where $C_8$ is 2-ethylhexyl.

2. The compound as claimed in claim 1 in which the symbol Y is O or S.

3. The compound as claimed in claim 1, characterized in that Y is R—C═C—R or R—C═N—.

4. The compound as claimed in claim 1, characterized in that b=0.

5. The compound as claimed in claim 1, wherein the radical Ar is benzene, toluene, xylene, fluorobenzene, difluorobenzene, diphenyl, tetraphenylene, naphthalene, fluorene, phenanthrene, anthracene, 1,3,5-triphenylbenzene, pyrene, perylene, chrysene, triptycene, [2.2]paracyclophane, pyridine, pyridazine, 4,5-benzo-pyridazine, pyrimidine, pyrazine, 1,3,5-triazine, pyrrole, indole, 1,2,5- or 1,3,4-oxadiazole, 2,2'- or 4,4'-diazabiphenyl, quinoline, 5,10H-dihydrophenazine, 10H-phenoxazine, phenothiazine, xanthene, 9-acridine, furan, benzofuran, thiophene or benzothiophene.

6. The compound as claimed in claim 1, wherein Ar is a phenyl, N-alkylphenoxazines, phenothiazine or xanthene or a mixture thereof.

7. The compound as claimed in claim 1, wherein Ar is phenyl, 1- or 2-naphthyl, 1-, 2- or 9-anthracenyl.

8. The compound as claimed in claim 1, characterized in that Q is F, Cl, Br, CN, $NO_2$ $SiR_3$ or a straight-chain or branched or cyclic alkyl or alkoxy group which has from 1 to 6 carbon atoms and in which one or more adjacent $CH_2$ groups optionally replaced by $—CF_2—$.

9. The compound as claimed in claim 1, characterized in that M=Ir.

10. The compound as claimed in claim 1, characterized in that c is greater than or equal to 1.

11. A process for preparing compounds as claimed in claim 1, by reacting compounds of the formula (III)

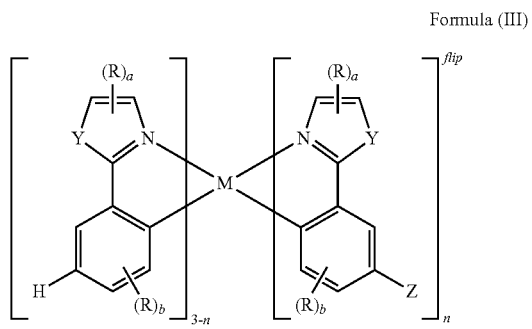

Formula (III)

where the symbols and indices M, X, Y, R, a, b and n are as defined in claim 1, and Z is Cl, Br or I, with an arylboronic acid or an arylboronic ester of the formula (V)

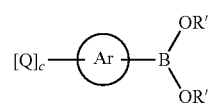

Formula (V)

where the symbols and indices Q, Ar and c are as defined in claim 1, and:
R' is identical or different on each occurrence and is H or an aliphatic or aromatic hydrocarbon radical having from 1 to 20 carbon atoms, where a plurality of substituents R' optionally forms a monocyclic or polycyclic ring system, in a reaction medium and in the presence of a transition metal or a transition metal compound, a phosphorus-containing or nitrogen-containing additive and a base.

12. The compound as claimed in claim 1, characterized in that its purity (determined by means of $^1$H-NMR and/or HPLC) is more than 99%.

13. A mixture of one or more compounds of the formula (I) and/or the formula (II) as claimed in claim 1, with an unconjugated, partially conjugated or conjugated polymer.

14. The mixture as claimed in claim 13, characterized in that the polymer is selected from the group consisting of polyfluorenes, polyspirobifluorenes, poly-para-phenylenes, polycarbazoles, polyvinylcarbazoles, polythiophenes and copolymers comprising a plurality of the units mentioned here.

15. The mixture as claimed in claim 13, characterized in that the polymer is soluble in organic solvents.

16. An electronic component comprising a compound as claimed in claim 1.

17. An organic electroluminescence and/or phosphorescence device which comprises the compound as claimed in claim 1.

18. An emission layer which comprises the compound as claimed in claim 1.

19. A solar cell or photovoltaic device which comprises the compound as claimed in claim 1.

20. The solar cell or photovoltaic device as claimed in claim 19, wherein the solar cell or photovoltaic device is an organic photodetector, an organic solar cell, in organic integrated circuits, in an organic field effect transistor, in an organic thin film transistor or in an organic solid-state laser.

* * * * *